(12) United States Patent
Hanauer et al.

(10) Patent No.: US 11,179,384 B2
(45) Date of Patent: Nov. 23, 2021

(54) TREATMENT OF NONALCOHOLIC FATTY LIVER DISEASE

(71) Applicant: TAKEDA GMBH, Constance (DE)

(72) Inventors: Guido Hanauer, Constance (DE); Hiroshi Nagabukuro, Fujisawa (JP); Yuichiro Amano, Fujisawa (JP)

(73) Assignee: TAKEDA GMBH, Constance (DE)

( * ) Notice: Subject to any disclaimer, the term of this patent is extended or adjusted under 35 U.S.C. 154(b) by 445 days.

(21) Appl. No.: 16/328,620

(22) PCT Filed: Aug. 25, 2017

(86) PCT No.: PCT/EP2017/071418
§ 371 (c)(1),
(2) Date: Feb. 26, 2019

(87) PCT Pub. No.: WO2018/037109
PCT Pub. Date: Mar. 1, 2018

(65) Prior Publication Data
US 2021/0283122 A1    Sep. 16, 2021

Related U.S. Application Data

(60) Provisional application No. 62/380,004, filed on Aug. 26, 2016.

(51) Int. Cl.
*A61K 31/473* (2006.01)
*A61P 3/10* (2006.01)
*A61P 1/16* (2006.01)
*A61P 3/06* (2006.01)

(52) U.S. Cl.
CPC ............. *A61K 31/473* (2013.01); *A61P 1/16* (2018.01); *A61P 3/06* (2018.01); *A61P 3/10* (2018.01)

(58) Field of Classification Search
CPC . A61K 31/473; A61P 1/16; A61P 3/06; A61P 3/10
See application file for complete search history.

(56) References Cited

U.S. PATENT DOCUMENTS 8,324,391 B2    12/2012  Kautz
2020/0179369 A1*  6/2020  Hanauer ............ A61P 13/12

FOREIGN PATENT DOCUMENTS

WO    WO 2001/060358 A1    8/2001
WO    WO 2009/109525 A1    9/2009
WO    WO 2017/017165 A1    2/2017

OTHER PUBLICATIONS

E. F. M. Wouters et al. "Effect of the Phosphodiesterase 4 Inhibitor Roflumilast on Glucose Metabolism in Patients with Treatment-Naïve, Newly Diagnosed Type 2 Diabetes Mellitus." *Journal of Clinical Endocrinology and Metabolism*, vol. 97, No. 9, Sep. 1, 2012, pp. E1720-E1725.
Fernandez-Martinez E. et al. "The thalidomide analog 3-phthalimido-3-(3,4-dimethoxyphenyl)-prop anoic acid improves the biliary cirrhosis in the rat." *Experimental and Toxicologic Pathology*, Jena, DE, vol. 61, No. 5, Dec. 17, 2008, pp. 471-479.
International Search Report for PCT/EP2017/071418, dated Mar. 1, 2018.
L. Gobejishvili et al. "Rolipram Attenuates Bile Duct Ligation-Induced Liver Injury in Rats: A Potential Pathogenic Role of PDE4." *Journal of Pharmacology and Experimental Therapeutics*, vol. 347, No. 1, Jul. 25, 2013, pp. 80-90.
Vollert S et al. "The glucose-lowering effects of the PDE4 inhibitors rofulilast and Yoflumilast—oxide inmice." Diabetologia; *Clinical and Experimental Diabetes and Metabolism*, Springer, Berlin, DE, vol. 55, No. 10, Jul. 13, 2012, pp. 2779-2788.

* cited by examiner

*Primary Examiner* — Timothy R Rozof
(74) *Attorney, Agent, or Firm* — Barnes & Thornburg LLP; Ryan L. Marshall; Jonathan Hartley

(57) ABSTRACT

The present invention is directed to methods for the treatment of non-alcoholic fatty liver disease (NAFLD) or non-alcoholic steato-hepatitis (NASH) with a phosphodiesterase 4 (PDE4) inhibitor.

17 Claims, 16 Drawing Sheets

Prophylactic effect of Compound A on hepatic fibrosis area. Compound A was administered to the mice for 7 weeks. Data are shown by mean ± SD (n=5-10). $^{\&}$P<0.05 vs. the mCDAA control by Shirley-Williams' test.

Prophylactic effect of Compound A on hepatic TG accumulation. Compound A was administered to the mice for 7 weeks. Data are shown by mean ± SD (n=5-10). #$P<0.05$ vs. the mCDAA control by Williams' test.

Effect of Compound A on plasma ALT level. Compound A was administered to the mice for 7 weeks. Data are shown by mean ± SD (n=5-10). #P<0.05 vs. the mCDAA control by Williams' test.

Effects of Compound A on body composition and food intake. Compound A was administered to the mice for 7 weeks. Data are shown by mean ± SD (n=5-10). #P<0.05 vs. the mCDAA control by Williams' test.

Therapeutic effect of Compound A on hepatic fibrosis area. Compound A was administered to the mice for 10 weeks starting from $6^{th}$ week of diet-feeding. Data are shown by mean ± SD (n=4-12). #P<0.05 vs. the mCDAA control by Williams' test.

Therapeutic effects of Compound A on hepatic TG accumulation. Compound A was administered to the mice for 10 weeks starting from $6^{th}$ week of diet-feeding. Data are shown by mean ± SD (n=4-12). $^{&}P<0.05$ vs. the mCDAA control by Shirley-Williams' test.

Effect of 28 days treatment with Compound A in male DIO mice on Body weight and total food intake: (A) and (B) represent the final body weight change after the 4 week treatment and total food intake for 4 weeks, respectively. Values are mean ± SD (n=6 and 7 for Veh (p.o.) and the other groups, respectively). #p≤0.025 compared to Veh (p.o.) by one-tailed Williams' test. Veh: Vehicle.

Effect of 28 days treatment with Compound A in male DIO mice on Fat Mass and Lean Mass: (A) and (B) show body fat mass and lean mass, respectively, before (Pre) and after (Post) the 4-week treatment. Values are mean ± SD (n=6 and 7 for Veh (p.o.) and the other groups, respectively). #$p \leq 0.025$ compared to Veh (p.o.) by one-tailed Williams' test. n.s.: not significant, Veh: Vehicle.

Effect of Compound A on HbA1c levels in female db/db mice after 28 days oral treatment: Values are presented as means ± SEM. Statistical differences were determined using one-way-ANOVA followed by a post-hoc analysis with Dunnet's correction (GraphPad Prism).

Definition of significance:    n.s.   = not significant ($p > 0.05$)

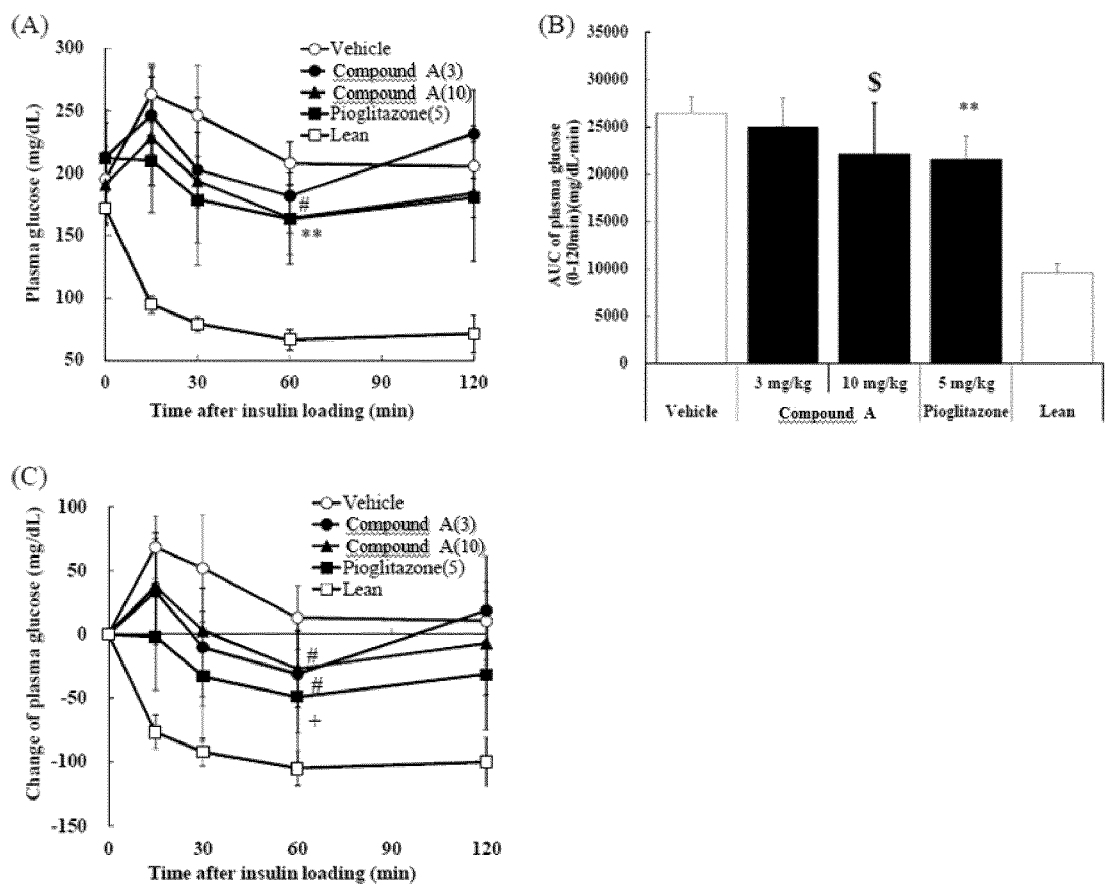

Effects of Compound A on insulin sensitivity in ob/ob mice after 29 days of treatment. Plasma glucose level (A) and changes in plasma glucose level from the zero time value (C) after insulin injection were monitored for 2 hours. Data in (B) represent AUC0-120 min of plasma glucose shown in (A). Values are mean and SD (ob/ob; n=8, Lean; n=5). In (A) and (C), statistical analysis was conducted on the data at 60 min after the insulin injection. #$p \leq 0.025$ compared to vehicle group by one-tailed Williams' test. \$$p \leq 0.025$ compared to vehicle group by Shirley-Williams test. +$p < 0.05$ compared to vehicle group by Aspin-Welch test. **$p \leq 0.01$ compared to vehicle group by Student's t-test.

Liver lipidosis of male C57BL/6J mice on high caloric (HFD) or standard diet (SD) before and after once daily administration of vehicle and Compound A (p.o.). Values as mean, n = 10, ***$p<0.001$ vs vehicle on standard diet (n=8-10)

Anti-fibrotic activity of Compound A in human hepatic stellate cells. Values are mean ± SD. The experiment was repeated 5 times.

Prophylactic effects of Compound A on hepatic gene expression (here: fibrosis related tissue inhibitor of metalloprotease-1 (TIMP-1)). Compound A was administered to the mice for 7 weeks. Data are shown by mean ± SD (n=5-10). *$P<0.05$ vs. the mCDAA control by Shirley-Williams' test.

Prophylactic effects of Compound A on hepatic gene expression (here: TNFα). Compound A was administered to the mice for 7 weeks. Data are shown by mean ± SD (n=5-10). *P<0.05 vs. the mCDAA control by Shirley-Williams' test.

Anti-fibrotic activity of Compound A in human THP-1 cells. Values are mean ± SD. The experiment was repeated 5 times.

LPS + Compound A p.o. [mg/kg]

Effect of Compound A on concentration of TNFα in plasma samples of LPS challenged Sprague Dawley rats. Results are shown by mean ± SD. Statistics: One-Way ANOVA with Dunnett's Post-Test, *$P<0.05$, $P<0.01$ and *$P<0.001$ vs. vehicle control.

TREATMENT OF NONALCOHOLIC FATTY LIVER DISEASE

CROSS REFERENCE TO RELATED APPLICATIONS

This application is a 371 national phase of PCT/EP2017/071418, filed Aug. 25, 2017, which claims the benefit of the filing date of U.S. Provisional Application No. 62/380,004, filed Aug. 26, 2016, the disclosures of which are incorporated, in their entirety, by this reference.

FIELD OF THE INVENTION

The present invention is directed to the treatment of Nonalcoholic Fatty Liver Disease. More particularly, the present invention is directed to treatment of Nonalcoholic Fatty Liver Disease with a phosphodiesterase 4 inhibitor (sometimes abbreviated as PDE4 inhibitor in the present specification).

BACKGROUND OF THE INVENTION

Non-alcoholic fatty liver disease (sometimes abbreviated as NAFLD in the present specification) is an increasingly common condition that has been linked to high calorie intake and an impaired glucose metabolism: 60-75% of patients with diabetes have NAFLD, and of these patients, approximately 10% progress to Nonalcoholic Steato-Hepatitis (sometimes abbreviated as NASH in the present specification). Of those diagnosed with NASH, approximately 20% will develop liver cirrhosis, and 40-60% of these patients will develop liver failure over 5-7 years. In addition, approximately 10% will develop hepato-cellular carcinoma (HCC) and approximately 30% will ultimately die from complications of their liver disease. There is currently no approved treatment available.

Under the term "Non-alcoholic fatty liver disease" (NAFLD) a spectrum of different forms and severity grades of pathologic liver fatty degeneration with varied prognosis is summarized. The spectrum includes on one hand the benign, non-progressive form of non-alcoholic fatty liver (sometimes abbreviated as NAFL in the present specification) and on the other hand, the non-alcoholic fatty-liver hepatitis or steatohepatitis (NASH), which is associated with liver inflammation and therefore can progress to liver fibrosis and liver cirrhosis.

In terms of diagnosis, NASH is usually first suspected in a person who is found to have elevations in liver tests that are included in routine blood test panels. Such liver tests include alanine aminotransaminase (ALT) or aspartate aminotransaminase (AST). When further evaluation shows no apparent reason for liver disease (such as medications, viral hepatitis, or excessive use of alcohol) and when x-rays or other imaging studies of the liver reveal the presence of fat, NASH is suspected. A definitive diagnosis of NASH and the dismissal of a diagnosis of simple fatty liver require a liver biopsy. A liver biopsy utilizes the insertion of a needle through the skin to remove a small sample of the liver. NASH is diagnosed when examination of the tissue reveals the presence of hepatic fat accumulation along with hepatic inflammation and hepatocyte abnormalities including ballooning. If the tissue shows fat deposition without other pathological findings, simple fatty liver or NAFL is diagnosed. An important piece of information learned from the biopsy is whether NASH has developed in the liver.

For diagnostic purposes, pathologists divide NAFLD into NAFL (predominantly macro vesicular steatosis with or without non-specific inflammation) and NASH. The histologic features of NASH include macro vesicular steatosis, ballooning degeneration of hepatocytes, scattered (mainly lobular) inflammation, apoptotic bodies and Mallory-Denk bodies. Notably, while some degree of fibrosis is often present, it is not necessary for the diagnosis. As opposed to NAFL, NASH has a specific pattern of liver injury that may be recognized even if present with other liver diseases. At early stages of disease, the histologic changes have a distinctive distribution with the most severe changes in acinar zone 3, which has the poorest oxygenation based on the anatomical localization. Because of the inherent disease complexity and the wide spectrum of findings, scoring systems were devised to aid pathologists in assessing the severity of NAFLD.

A separate system of scoring the features of NAFLD, termed the NAFLD Activity Score (sometimes abbreviated as NAS in the present specification) has been developed as a tool to measure changes in NAFLD during therapeutic trials. The score is defined as the unweighted sum of the scores for steatosis (0-3), lobular inflammation (0-3), and ballooning (0-2), thus ranging from 0-8. Fibrosis is not included since it is believed to be a more irreversible parameter.

A NAFLD activity score >4 is considered to have optimal sensitivity and specificity for predicting steato-hepatitis, and is the recommended value for admission into an interventional trial for NASH. In the diagnosis using the NAS, NAFLD is diagnosed by a NAS of at most 3, and NASH is diagnosed by a NAS of at least 5. A NAS score of more than 3 and less than 5 (typically 4) is generally diagnosed to be borderline NASH.

NAFLD and NASH are emerging as common, clinically important type of chronic liver disease in industrialized countries. The management of NAFLD and/or NASH is largely conservative and includes diet and exercise, and treatment with weight reduction drugs as well as lipid-lowering agents and several antioxidant approaches (e.g. vitamins, glutathione). No established treatment currently exists for these potentially serious disorders.

Thus, there is still a high demand for novel and effective medicaments for the treatment of NAFLD and in particular for the treatment of NASH.

SUMMARY OF THE INVENTION

In a first aspect the present invention provides a method for the treatment of Nonalcoholic Fatty Liver Disease (NAFLD) in a mammal in need of such treatment, comprising administering to the mammal suffering from Nonalcoholic Fatty Liver Disease (NAFLD) a therapeutically effective amount of a phosphodiesterase 4 inhibitor.

In a second aspect the present invention provides a method for the treatment of non-alcoholic steato-hepatitis (NASH) in a mammal in need of such treatment, comprising administering to the mammal suffering from non-alcoholic steato-hepatitis (NASH) a therapeutically effective amount of a phosphodiesterase 4 inhibitor.

In a third aspect the present invention provides a method for the concomitant treatment of diabetes mellitus type 2 and non-alcoholic fatty liver disease (NAFLD), comprising administering to the mammal suffering from diabetes mellitus type 2 and nonalcoholic fatty liver disease a therapeutically effective amount of a phosphodiesterase 4 inhibitor.

In a fourth aspect the present invention provides a method for the concomitant treatment of diabetes mellitus type 2 and non-alcoholic steato-hepatitis (NASH), comprising administering to the mammal suffering from diabetes mellitus type 2 and non-alcoholic steato-hepatitis (NASH) a therapeutically effective amount of a phosphodiesterase 4 inhibitor.

The phosphodiesterase 4 inhibitor is selected from 5-((2R,4aR,10bR)-9-Ethoxy-2-hydroxy-8-methoxy-1,2,3,4,4a,10b-hexahydro-phenanthridin-6-yl)1-methyl-1H-pyridin-2-one (hereinafter referred to as "Compound A") and a pharmaceutically acceptable salt thereof.

The details of one or more aspects of the invention and its embodiments are set forth in the accompanying figures and description below. Other features and advantages will become apparent from the description, the figures and the claims.

BRIEF DESCRIPTION OF THE FIGURES

FIG. 10: Effect of Compound A on insulin sensitivity in ob/ob mice after 29 days of treatment

DEFINITIONS

Figure 1:
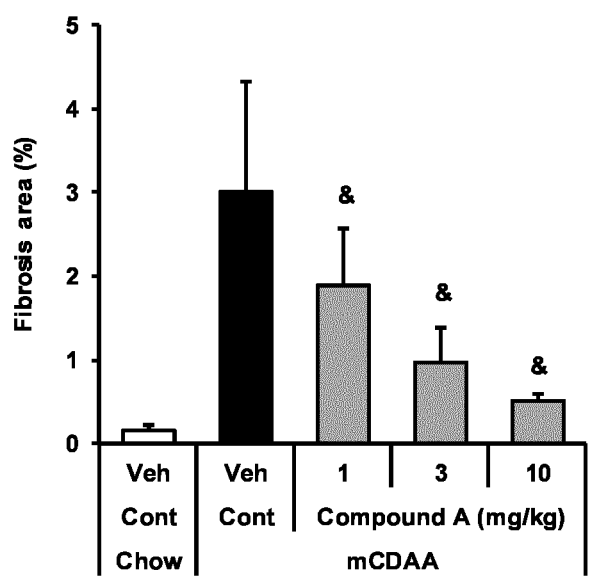
FIG. 1: Prophylactic effects of Compound A on hepatic fibrosis area in a mouse model (Homozygous LDLR-KO mice) of NASH

In the present invention, the phrase "therapeutically effective amount" refers to the amount of active compound or pharmaceutical agent that elicits the biological or medicinal response that is being sought in a tissue, system, animal, individual, or human, by the researcher, veterinarian, medical doctor or other clinician, which includes one or more of the following:

Ameliorating the disease or inhibiting the disease and its progression; for example, ameliorating/inhibiting a disease, condition or disorder in an individual who is displaying the pathology or symptomatology of the disease, condition or disorder (i.e., arresting further development of the pathology and/or symptomatology or even reversing the pathology and/or symptomatology), such as in case of NAFLD and/or NASH, for example, by decreasing one or more of (a) body weight, (b) body fat, (c) liver fat content, (d) levels of serum alanine transaminase (ALT) or serum aspartate transaminase (AST), (e) fibrosis in the liver and by (f) improving insulin resistance as well as type 2 diabetes mellitus.

As used herein, "mammal" refers to humans, mice, rats, rabbits, dogs, cats, bovines, horses, swine and monkeys, with preference given to humans.

As used herein, "pharmaceutically acceptable salt" refers to salts with bases and salts with acids.

DETAILED DESCRIPTION OF THE INVENTION

The present invention provides a method for the treatment of Nonalcoholic Fatty Liver Disease (NAFDL) comprising administering to a patient suffering from Nonalcoholic Fatty Liver Disease (NAFDL) a therapeutically effective amount of a phosphodiesterase 4 inhibitor.

The present invention also provides a method for the treatment of non-alcoholic steato-hepatitis (NASH) comprising administering to a patient suffering from non-alcoholic steato-hepatitis (NASH) a therapeutically effective amount of a phosphodiesterase 4 inhibitor.

Furthermore the present invention provides a method for the concomitant treatment of diabetes mellitus type 2 and non-alcoholic fatty liver disease (NAFLD), comprising administering to the mammal suffering from diabetes mellitus type 2 and nonalcoholic fatty liver disease (NAFLD) a therapeutically effective amount of a phosphodiesterase 4 inhibitor.

As well, the present invention provides a method for the concomitant treatment of diabetes mellitus type 2 and non-alcoholic steato-hepatitis (NASH), comprising administering to the mammal suffering from diabetes mellitus type 2 and non-alcoholic steato-hepatitis (NASH) a therapeutically effective amount of a phosphodiesterase 4 inhibitor.

The phosphodiesterase 4 inhibitor is selected from 5-((2R,4aR,10bR)-9-Ethoxy-2-hydroxy-8-methoxy-1,2,3,4,4a,10b-hexahydro-phenanthridin-6-yl)1-methyl-1H-pyridin-2-one and a pharmaceutically acceptable salt thereof.

The chemical name of 5-((2R,4aR,10bR)-9-Ethoxy-2-hydroxy-8-methoxy-1,2,3,4,4a,10b-hexahydro-phenanthridin-6-yl)-1-methyl-1H-pyridin-2-one is for ease of reading at many occasions throughout this specification and the claims replaced by the expression "Compound A".

Compound A is disclosed in U.S. Pat. No. 8,324,391, which is hereby incorporated by reference in its entirety.

Examples of pharmaceutically acceptable salts of Compound A are disclosed in U.S. Pat. No. 8,754,218, which is hereby incorporated by reference in its entirety, too. Examples of pharmaceutically acceptable salts of Compound A, which may be mentioned are the hydrochloride, the fumarate, the L-tartrate, the edisilate, the esilate, the hydrobromide and the tosylate salt of Compound A. Compound A is preferably used in its free form rather than in the form of a pharmaceutically acceptable salt thereof.

Compound A may be synthesized, for example, as disclosed in U.S. Pat. No. 8,324,391.

Compound A is a very potent and selective PDE4 inhibitor. In addition, Compound A has a very favorable pharmacokinetic profile.

In several in vitro and in vivo (animal) experiments it has been found that Compound A shows strong ameliorating effects on parameters relevant for the treatment of non-alcoholic fatty liver disease (NAFLD) and/or non-alcoholic steato-hepatitis (NASH), such as for example, decrease of body weight, decrease of body fat mass, decrease of serum alanine transaminase (ALT), decrease of liver fat content, decrease of fibrosis in the liver and improvement of insulin resistance.

Compound A differs from other development candidates intended for the treatment of NAFLD/NASH in that it exerts its effects via anti-inflammatory, anti-fibrotic and anti-steatotic mode of action. It is believed that Compound A has a superior safety/tolerability profile compared to other (second generation?) PDE4 inhibitors. It is furthermore believed that all of these effects observed in in vitro and animal experiments will translate in corresponding effects in the clinical setting in humans. In fact, Compound A did show a very favorable safety and pharmacokinetic profile in Phase 1 clinical studies [single rising dose (dosing 0.05 to 0.85 mg) and multiple rising dose (dosing 0.05 to 0.8 mg for 7 days; dosing 0.35 and 0.8 mg for up to 14 days)]; in these clinical trials no PDE4 inhibitor specific adverse events, such as for example diarrhea and nausea have been observed.

In a first aspect the invention relates to a method for the treatment of non-alcoholic fatty liver disease (NAFLD), comprising administering to a mammal (patient) in need thereof a therapeutically effective amount of a phosphodiesterase 4 (PDE4) inhibitor, wherein the phosphodiesterase 4 (PDE4) inhibitor is selected from the group consisting of Compound A and a pharmaceutically acceptable salt thereof.

In a second aspect the invention relates to a method for the treatment of non-alcoholic steato-hepatitis (NASH), comprising administering to a mammal (patient) in need thereof a therapeutically effective amount of a phosphodiesterase 4 (PDE4) inhibitor, wherein the phosphodiesterase 4 (PDE4) inhibitor is selected from the group consisting of Compound A and a pharmaceutically acceptable salt thereof.

In a third aspect the invention relates to a method for the concurrent treatment of diabetes mellitus type 2 and non-alcoholic fatty liver disease (NAFLD), comprising administering to a mammal (patient) suffering from diabetes mellitus type 2 and non-alcoholic fatty liver disease a therapeutically effective amount of a phosphodiesterase 4 (PDE4) inhibitor, wherein the phosphodiesterase 4 (PDE4) inhibitor is selected from the group consisting of Compound A and a pharmaceutically acceptable salt thereof.

In a fourth aspect the invention relates to a method for the concurrent treatment of diabetes mellitus type 2 and non-alcoholic steato-hepatitis (NASH), comprising administering to a mammal (patient) suffering from diabetes mellitus type 2 and non-alcoholic steato-hepatitis (NASH) a therapeutically effective amount of a phosphodiesterase 4 (PDE4) inhibitor, wherein the phosphodiesterase 4 (PDE4) inhibitor is selected from the group consisting of Compound A and a pharmaceutically acceptable salt thereof.

In a preferred embodiment of the invention the phosphodiesterase 4 (PDE4) inhibitor is Compound A.

The present invention provides a method for the treatment of non-alcoholic fatty liver disease (NAFLD), respectively non-alcoholic steato-hepatitis (NASH) comprising administering Compound A or a pharmaceutical acceptable salt thereof to the mammal (patient) in need of treatment; Compound A or a pharmaceutically acceptable salt thereof may be administered by a variety of administration routes.

Administration can be, for example, pulmonary, oral, parenteral or transdermal. The preferred route of administration is oral.

The preferred dosage form is the oral dosage form. Suitable oral dosage forms include, but are not limited to tablets, capsules, powders, pills, solutions, suspensions, emulsions, pastes and granules. The most preferred oral dosage form is a tablet.

Dosage Information

Compound A or a pharmaceutically acceptable salt thereof may be administered once daily, twice daily or three times a day.

Compound A may be administered in an oral dosage form comprising Compound A in any amount from 0.1 mg to 6 mg (preferred in any amount from 0.8 to 3.25 mg), such as, but not limited to 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 or 6 mg, of which 0.8, 0.9, 1, 1.25, 1.5, 1.75, 2, 2.25, 2.5, 2.75, 3 and 3.25 mg are preferred.

As indicated above, the oral dosage form comprising Compound A in any amount between 0.1 and 6 mg (preferred in any amount between 0.8 and 3.25 mg) may be administered once daily, twice daily or three times a day, of which twice daily and three times a day administration are preferred and twice daily administration is particularly preferred.

Corresponding amounts of a pharmaceutically acceptable salt of Compound A can easily be calculated by one of ordinary skill, depending on the choice of the respective salt.

In an embodiment of the first aspect of the invention Compound A is administered once daily at a dose of between 0.1 mg and 6 mg or a pharmaceutically acceptable salt of Compound A is administered at a daily dose corresponding to the Compound A once daily dose of between 0.1 mg and 6 mg.

In another embodiment of the first aspect of the invention Compound A is administered twice daily at a dose of between 0.1 mg and 6 mg or a pharmaceutically acceptable salt of Compound A is administered twice daily at a dose corresponding to the Compound A twice daily dose of between 0.1 mg and 6 mg.

In another embodiment of the first aspect of the invention Compound A is administered three times a day at a dose of between 0.1 mg and 6 mg or a pharmaceutically acceptable salt of Compound A is administered three times a day at a dose corresponding to the Compound A three times a day dose of between 0.1 mg and 6 mg.

In another embodiment of the first aspect of the invention Compound A is administered once daily at a dose of between 0.8 mg and 3.25 mg or a pharmaceutically acceptable salt of Compound A is administered once daily at a dose corresponding to the Compound A once daily dose of between 0.8 mg and 3.25 mg.

In another embodiment of the first aspect of the invention Compound A is administered twice daily at a dose of between 0.8 mg and 3.25 mg or a pharmaceutically acceptable salt of Compound A is administered twice daily at a dose corresponding to the Compound A twice daily dose of between 0.8 mg and 3.25 mg.

In another embodiment of the first aspect of the invention Compound A is administered three times a day at a dose of between 0.8 mg and 3.25 mg or a pharmaceutically acceptable salt of Compound A is administered three times a day at a dose corresponding to the Compound A three times a day dose of between 0.8 mg and 3.25 mg.

In another embodiment of the first aspect of the invention Compound A is administered once daily at a dose of between 0.1 mg and 2 mg or a pharmaceutically acceptable salt of Compound A is administered once daily at a dose corresponding to the Compound A once daily dose of between 0.1 mg and 2 mg.

In an embodiment of the second aspect of the invention Compound A is administered once daily at a dose of between 0.1 mg and 6 mg or a pharmaceutically acceptable salt of Compound A is administered once daily at a dose corresponding to the Compound A once daily dose of between 0.1 mg and 6 mg.

In another embodiment of the second aspect of the invention Compound A is administered twice daily at a dose of between 0.1 mg and 6 mg or a pharmaceutically acceptable salt of Compound A is administered twice daily at a dose corresponding to the Compound A twice daily dose of between 0.1 mg and 6 mg.

In another embodiment of the second aspect of the invention Compound A is administered three times a day at a dose of between 0.1 mg and 6 mg or a pharmaceutically acceptable salt of Compound A is administered three times a day at a dose corresponding to the Compound A three times a day dose of between 0.1 mg and 6 mg.

In another embodiment of the second aspect of the invention Compound A is administered once daily in an oral dosage form comprising Compound A in an amount of between 0.8 mg and 3.25 mg or comprising the pharmaceutically acceptable salt of Compound A in an amount corresponding to the amount of Compound A of between 0.8 mg and 3.25 mg.

In another embodiment of the second aspect of the invention Compound A is administered twice daily at a dose of between 0.8 mg and 3.25 mg or a pharmaceutically acceptable salt of Compound A is administered twice daily at a dose corresponding to the Compound A twice daily dose of between 0.8 mg and 3.25 mg.

In another embodiment of the second aspect of the invention Compound A is administered three times a day at a dose between 0.8 mg and 3.25 mg or a pharmaceutically acceptable salt of Compound A is administered three times a day at a dose corresponding to the Compound A three times a day dose of between 0.8 mg and 3.25 mg.

In another embodiment of the second aspect of the invention Compound A is administered once daily at a dose of between 0.1 mg and 2 mg or a pharmaceutically acceptable salt of Compound A is administered once daily at a dose corresponding to the Compound A once daily dose of between 0.1 mg and 2 mg.

In an embodiment of the third aspect of the invention Compound A is administered once daily at a dose of between 0.1 mg and 6 mg or a pharmaceutically acceptable salt of Compound A is administered once daily at a dose corresponding to the Compound A once daily dose of between 0.1 mg and 6 mg.

In another embodiment of the third aspect of the invention Compound A is administered twice daily at a dose of between 0.1 mg and 6 mg or a pharmaceutically acceptable salt of Compound A is administered at a dose corresponding to the Compound A twice daily dose of between 0.1 mg and 6 mg.

In another embodiment of the third aspect of the invention Compound A is administered three times a day at a dose of between 0.1 mg and 6 mg or a pharmaceutically acceptable salt of Compound A is administered three times a day at a dose corresponding to the Compound A three times a day dose of between 0.1 mg and 6 mg.

In another embodiment of the third aspect of the invention Compound A is administered once daily at a dose of between 0.8 mg and 3.25 mg or a pharmaceutically acceptable salt of Compound A is administered once daily at a dose corresponding to the Compound A once daily dose of between 0.8 mg and 3.25 mg.

In another embodiment of the third aspect of the invention Compound A is administered twice daily at a dose of between 0.8 mg and 3.25 mg or a pharmaceutically acceptable salt of Compound A is administered twice daily at a dose corresponding to the Compound A twice daily dose of between 0.8 mg and 3.25 mg.

In another embodiment of the third aspect of the invention Compound A is administered three times a day at a dose of between 0.8 mg and 3.25 mg or a pharmaceutically acceptable salt of Compound A is administered three times a day at a dose corresponding to the Compound A three times a day dose of between 0.8 mg and 3.25 mg.

In another embodiment of the third aspect of the invention Compound A is administered once daily at a dose of between 0.1 mg and 2 mg or a pharmaceutically acceptable salt of Compound A is administered once daily at a dose corresponding to the Compound A once daily dose of between 0.1 mg and 2 mg.

In an embodiment of the fourth aspect of the invention Compound A is administered once daily at a dose of between 0.1 mg and 6 mg or a pharmaceutically acceptable salt of Compound A is administered once daily at a dose corresponding to the Compound A once daily dose of between 0.1 mg and 6 mg.

In another embodiment of the fourth aspect of the invention Compound A is administered twice daily at a dose of between 0.1 mg and 6 mg or a pharmaceutically acceptable salt of Compound A is administered twice daily at a dose corresponding to the Compound A twice daily dose of between 0.1 mg and 6 mg.

In another embodiment of the fourth aspect of the invention Compound A is administered three times a day at a dose of between 0.1 mg and 6 mg or a pharmaceutically acceptable salt of Compound A is administered three times a day at a dose corresponding to the Compound A three times a day dose of between 0.1 mg and 6 mg.

In another embodiment of the fourth aspect of the invention Compound A is administered once daily at a dose of between 0.8 mg and 3.25 mg or a pharmaceutically acceptable salt of Compound A is administered once daily at a dose corresponding to the Compound A once daily dose of between 0.8 mg and 3.25 mg.

In another embodiment of the fourth aspect of the invention Compound A is administered twice daily at a dose of between 0.8 mg and 3.25 mg or a pharmaceutically acceptable salt of Compound A is administered twice daily at a dose corresponding to the Compound A twice daily dose of between 0.8 mg and 3.25 mg.

In another embodiment of the fourth aspect of the invention Compound A is administered three times a day at a dose of between 0.8 mg and 3.25 mg or a pharmaceutically acceptable salt of Compound A is administered three times a day at a dose corresponding to the Compound A three times a day dose of between 0.8 mg and 3.25 mg.

In another embodiment of the fourth aspect of the invention Compound A is administered once daily at a dose of between 0.1 mg and 2 mg or a pharmaceutically acceptable salt of Compound A is administered once daily at a dose corresponding to the Compound A once daily dose of between 0.1 mg and 2 mg.

In a fifth aspect the invention relates to the treatment of non-alcoholic steato-hepatitis (NASH) comprising administering a therapeutically effective amount of Compound A or a pharmaceutically acceptable salt thereof to a patient in need thereof, not adequately controlled despite one or more of the loss of excess weight,
incorporation of a balanced diet,
adequate physical activity,
avoidance of alcohol and
treatment with an antioxidant, such as for example, Vitamin E.

In a preferred embodiment of the first, second, third, fourth or fifth aspect of the invention the phosphodiesterase 4 (PDE4) inhibitor is Compound A.

In another preferred embodiment of the first, second, third, fourth or fifth aspect of the invention Compound A or the pharmaceutical salt of Compound A is administered in an oral dosage form.

Pharmaceutical Formulations and Dosage Forms

When employed as pharmaceutical, Compound A or a pharmaceutically acceptable salt thereof (sometimes collectively referred to as "the compounds of the invention" in the present specification) can be administered in the form of pharmaceutical composition(s). These pharmaceutical composition(s) can be prepared in a manner well known in the pharmaceutical art and can be administered by a variety of routes. Administration can be pulmonary (e.g., by inhalation or insufflation of powders or aerosols, including by nebulizer), intratracheal, intranasal, epidermal and transdermal, oral or parenteral. Parenteral administration includes intravenous, subcutaneous, intraperitoneal or intramuscular injection, or infusion. Parenteral administration can be in the form of a single bolus dose or for example, can be by a continuous perfusion pump. The preferred route of administration is oral.

Pharmaceutical composition(s) and formulations for topical administration can include: transdermal patches; conventional pharmaceutical carriers; aqueous, powder or oily bases; thickeners; and/or the like which may be necessary or desirable.

This invention also includes pharmaceutical composition(s) which contain, as the active ingredient, a compound of the invention in combination with one or more pharmaceutically acceptable carriers. Pharmaceutically acceptable carriers known in the art can be employed. In making the pharmaceutical composition(s) of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the pharmaceutical composition(s) can be in the form of tablets, pills, powders, lozenges, sachets, cachets, elixirs, suspensions, emulsions, solutions, syrups, aerosols (as a solid or in a liquid medium), soft and hard gelatin capsules, suppositories, sterile injectable solutions, and sterile packaged powders.

The pharmaceutical composition(s) can be formulated in a unit dosage form, each dosage containing an amount of the active ingredient as described above. The term "unit dosage forms" refers to physically discrete units suitable as unitary dosages for human subjects and other mammals, each unit containing a predetermined quantity of active ingredient calculated to produce the desired therapeutic effect, in association with a suitable pharmaceutical excipient.

The compound of the invention is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

Pre-Clinical Studies

1) Prophylactic Effects of Compound A in a Mouse Model of NASH

Prophylactic effects of Compound A on parameters such as a) hepatic fibrosis formation, b) hepatic triglyceride formation and c) plasma ALT reduction were examined in a rodent model of NASH.

Homozygous low-density lipoprotein receptor knockout (LDLR-KO) mice were fed with chow or modified choline deficient, L-amino acid-defined (mCDAA) diet (A08111307, Research Diets, USA). After 1 week under chow or mCDAA diet, the mice were orally dosed with Compound A (1, 3 and 10 mg/5 ml/kg, QD, n=10; suspension in 0.5 w/v % methylcellulose suspension) for 7 weeks.

Figure 2:
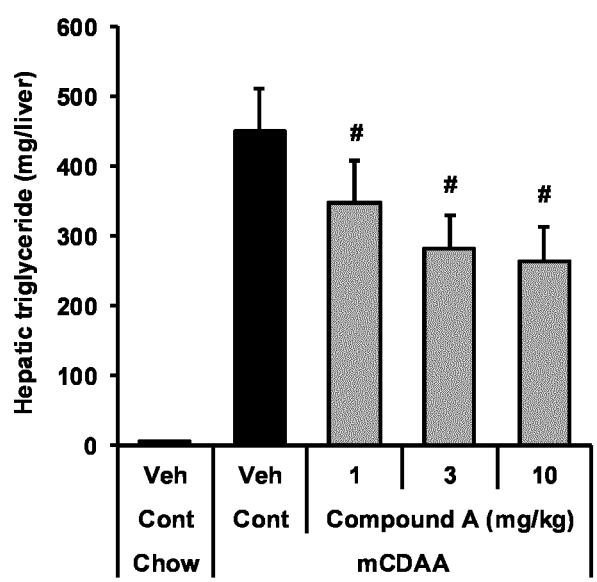
FIG. 2: Prophylactic effects of Compound A on hepatic TG accumulation in a mouse model (Homozygous LDLR-KO mice) of NASH
Figure 3:
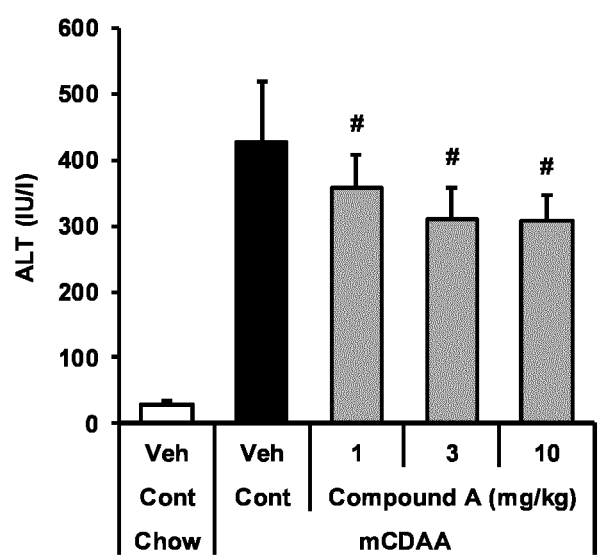
FIG. 3: Effect of Compound A on plasma ALT level in a mouse model (Homozygous LDLR-KO mice) of NASH

Treatment with Compound A (1, 3, and 10 mg/5 ml/kg, QD, n=10) resulted in dose-dependent reduction of hepatic fibrosis area (FIG. 1). Hepatic triglyceride (TG) content (FIG. 2) and plasma ALT levels (FIG. 3) were also significantly reduced.

Figure 4:
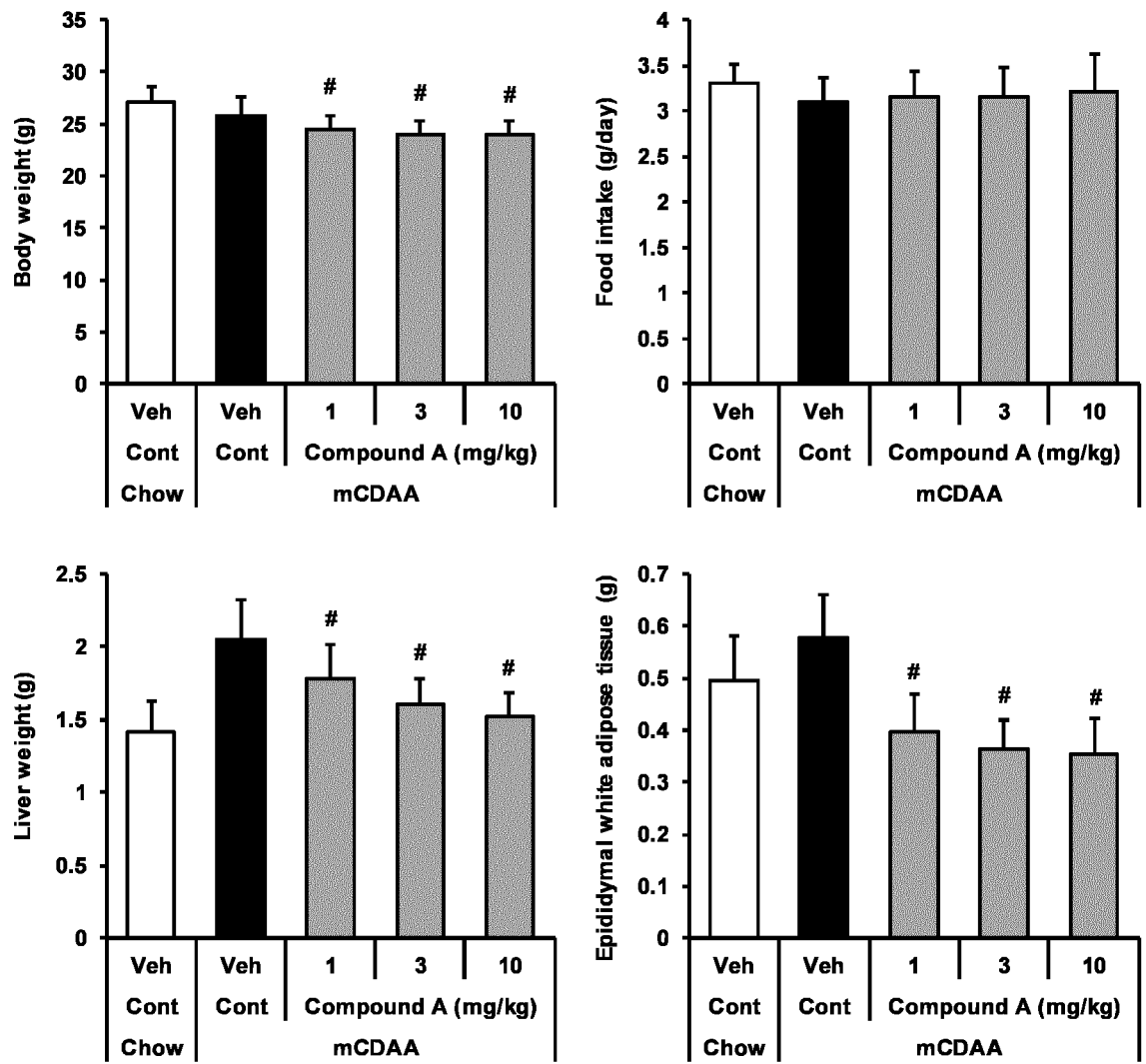
FIG. 4: Effect of Compound A on body composition and food intake in a mouse model (Homozygous LDLR-KO mice) of NASH

Body weight was slightly decreased, while no change in food intake was observed. Liver weight and epididymal white adipose tissue (which represents a surrogate for body fat mass) were dose dependently decreased (FIG. 4).

In addition prophylactic effects of Compound A on hepatic gene expression were evaluated. After total RNA was extracted from liver, cDNA was amplified using High-Capacity cDNA Reverse Transcription Kit (ABI 4368813), and target gene mRNA was measured using Taqman PCR. The target gene expression level was normalized by GAPDH.

Figure 13:
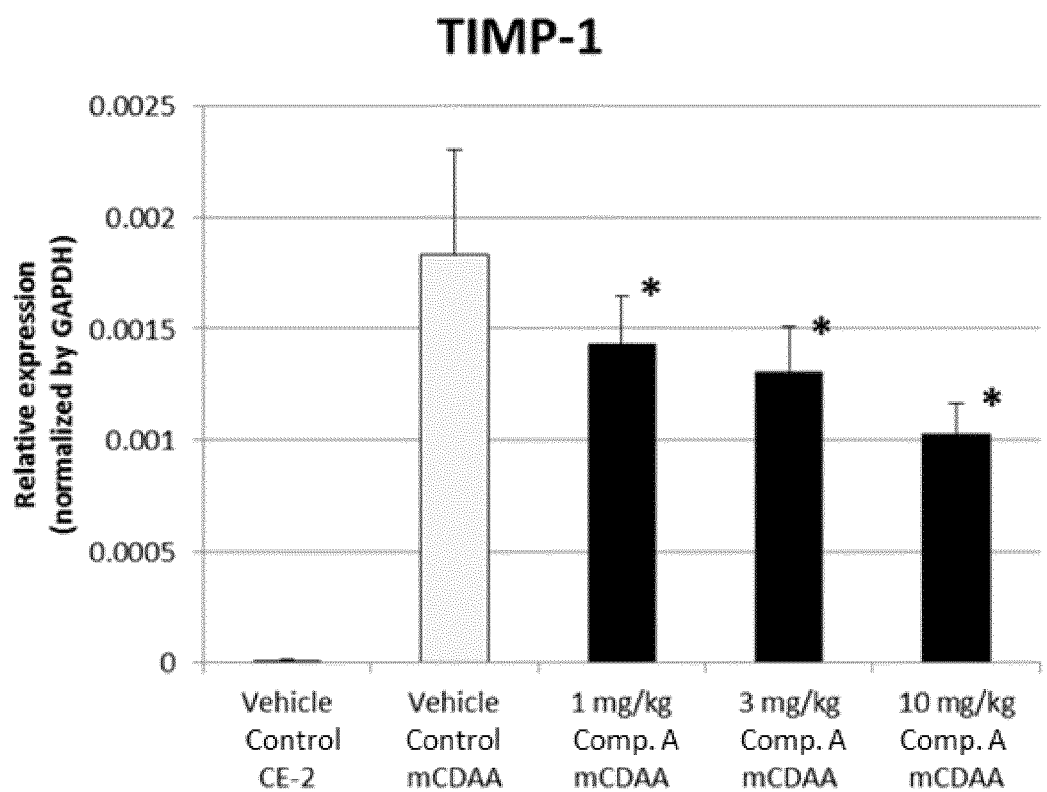
FIG. 13: Prophylactic effects of Compound A on hepatic gene expression—TIMP-1
Figure 14:
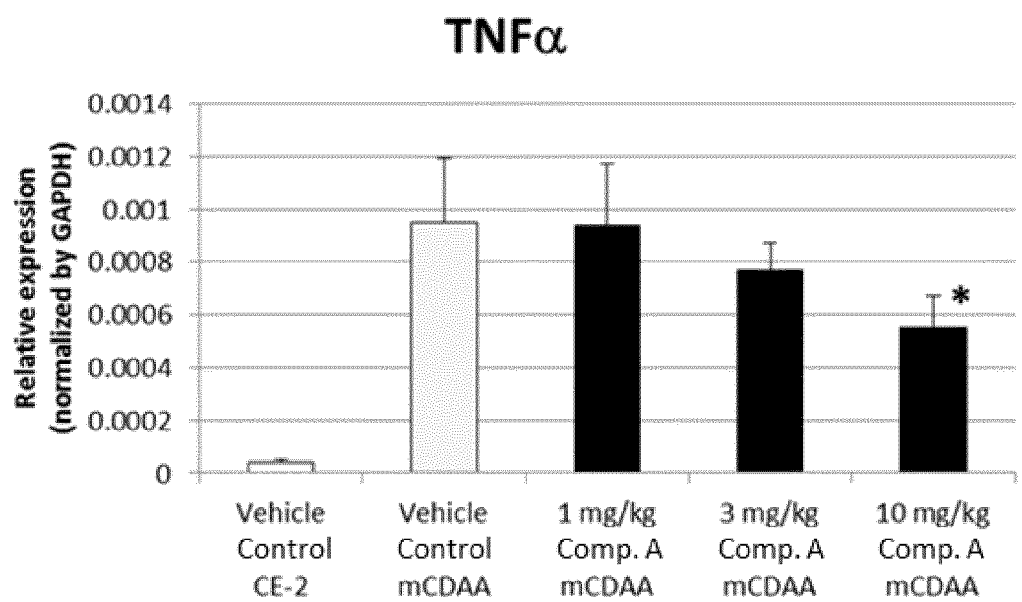
FIG. 14: Prophylactic effects of Compound A on hepatic gene expression—TNFα

Treatment with Compound A resulted in dose-dependent reduction of hepatic fibrosis-related tissue inhibitor of metalloproteases-1 (TIMP-1) gene expression (FIG. 13) and hepatic inflammatory TNFα gene expression (FIG. 14).

These data all together suggest that Compound A prevented NASH progression by its anti-inflammatory, and anti-fibrotic effect in the liver.

2) Therapeutic Effects of Compound A in a Mouse Model of NASH

To evaluate therapeutic potential of Compound A, effects of Compound A were additionally examined after hepatic fibrosis formation. Homozygous LDLR-KO mice were fed with chow or mCDAA diet (A08111307, Research Diets, USA). After 6 week under chow or mCDAA diet, the mice were orally dosed with Compound A (4, and 8 mg/5 mL/kg, QD, n=12; suspension in 0.5 w/v % methylcellulose solution) for 10 weeks.

Figure 5:
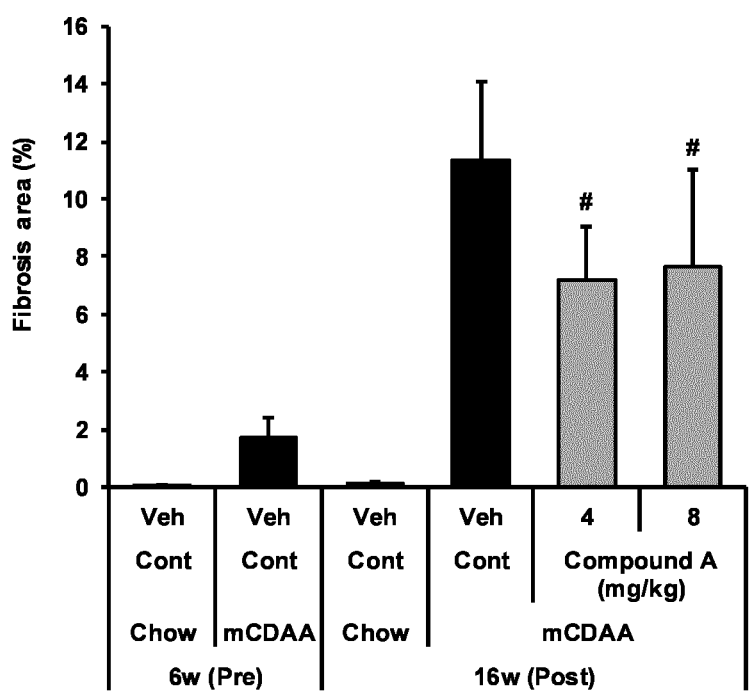
FIG. 5: Therapeutic effects of Compound A on hepatic fibrosis area in a mouse model (Homozygous LDLR-KO mice) of NASH
Figure 6:
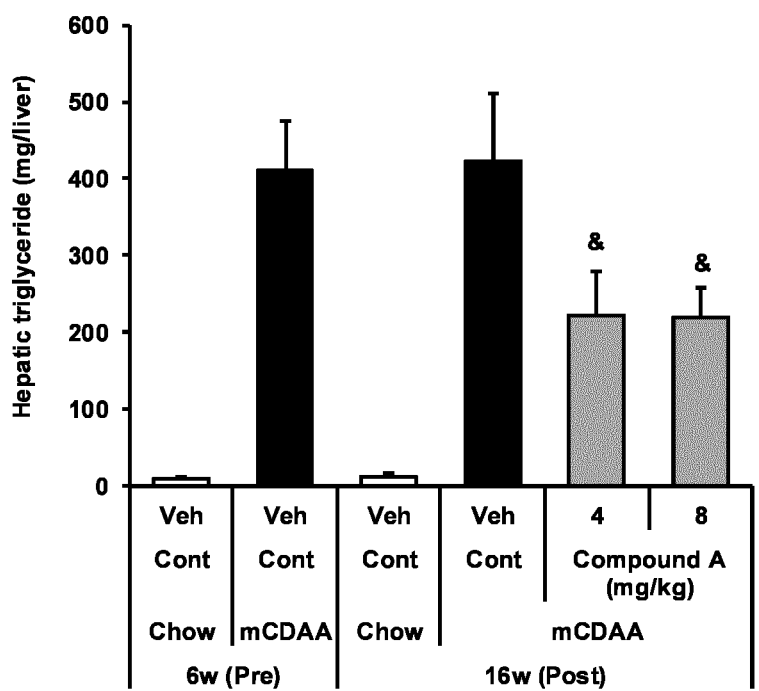
FIG. 6: Therapeutic effects of Compound A on hepatic TG accumulation in a mouse model (Homozygous LDLR-KO mice) of NASH

At $6^{th}$ week point when starting the Compound A treatment, hepatic fibrosis formation and hepatic triglyceride accumulation, (FIGS. 5 and 6). Treatment with Compound A resulted in reduction of hepatic fibrosis area (FIG. 5); hepatic TG content was also significantly reduced from the initial value (FIG. 6). These data suggest therapeutic potential of Compound A for existing fibrosis and steatosis.

3) Effect on Body Weight and Fat and Lean Mass of Compound A—4 Weeks Treatment in Diet-Induced Obese (DIO) Mice Model Description Male C57BL/6J mice were obtained from CLEA Japan, Inc. The mice were fed High fat diet D12451 (Research diets, Inc) from 5 week to 54-week old and water ad libitum.

Experimental Protocol

All mice were housed individually in animal cages and used for the study after 2 weeks of acclimation period. Animal groups (n=7) were treated with either vehicle (0.5 w/v % methylcellulose, p.o.) or Compound A (1 mg/kg or 3 mg/kg, p.o. suspension in 0.5 w/v % methylcellulose solution) in the evening once a day for 4 weeks from 50 weeks of age. Body weight was measured 2 or 3 times per week. Regarding body composition fast mass and lean mass were measured.

Measurements

Body composition (fat mass and lean mass) was measured by Echo-MRI-900 (ALOKA Japan).

Statistical Analysis

All data are presented as mean±S.D. For evaluation of the effects of Compound A, statistical significances between vehicle (p.o.) and Compound A treated groups were analyzed with one-tailed Williams' test or Shirley-Williams test when the variances among the groups were homogeneous or heterogeneous, respectively. The p-values less than 0.025 were considered statistically significant in one-tailed Williams' test or Shirley-Williams test. Body weight change from pretreatment (Day 0) was calculated using the following formula: [(BW-BW at Day 0)/BW at Day 0]×100.

Results

Figure 7:
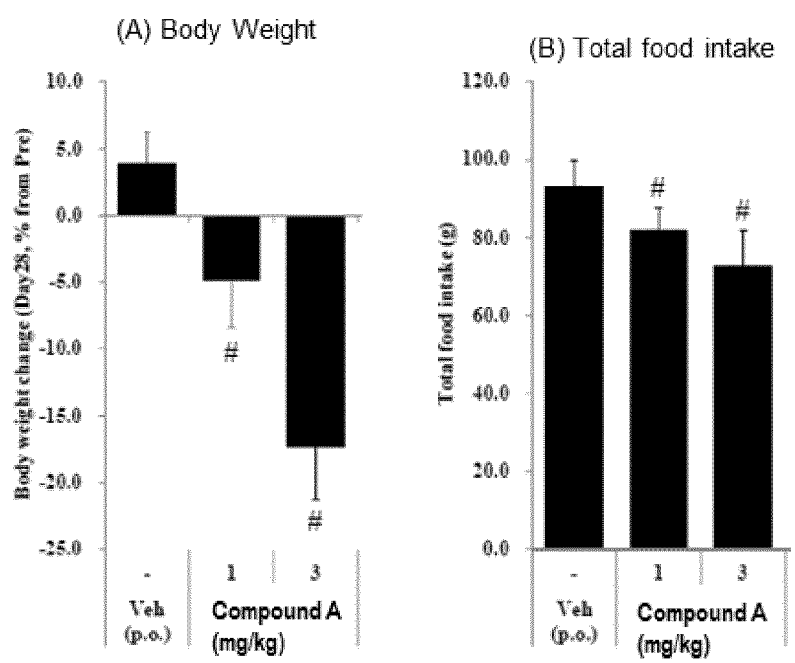
FIG. 7: Effect of 28 days treatment with Compound A in male DIO mice on Body weight and total food intake
Figure 8:
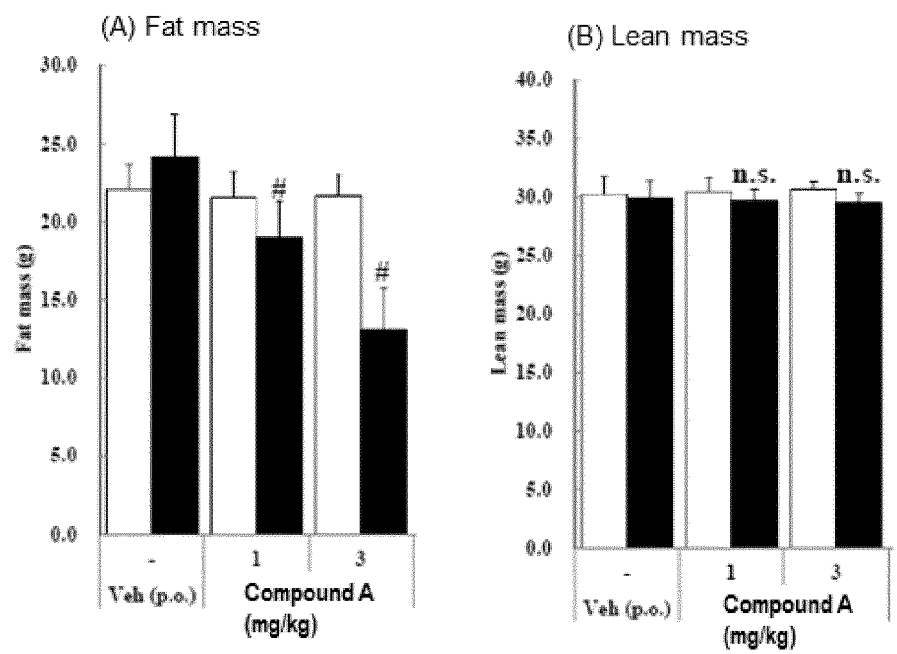
FIG. 8: Effect of 28 days treatment with Compound A in male DIO mice on fat mass and lean mass

Four week-treatment with Compound A (1 and 3 mg/kg) in DIO mice dose-dependently and significantly decreased body weight (1 mg/kg; −4.9±3.5%, 3 mg/kg; −17.2±4.0%) compared to vehicle (p.o.) treated group (+3.8%±2.4%). Compound A showed a durable body weight lowering effect during the 4-week study period (FIG. 7). When corrected with vehicle (p.o.)-treated body weight change, Compound A (1 mg/kg) showed body weight reduction by −8.7±3.5%. Treatment with Compound A (1 and 3 mg/kg) dose dependently and significantly decreased fat mass (FIG. 8A) without affecting lean mass (FIG. 8B), suggesting that the body weight lowering effect of Compound A was derived from the specific reduction of fat mass.

4. Compound A—Effect on HbA1c—4 Weeks Treatment in Db/Db Mice

Model Description

Female db/db mice were purchased from Taconic (Lille Skensved, Denmark) at 5-6 weeks of age and were maintained under standard conditions (5 animals/cage; 12 h light-dark cycle; room temperature of 22±2° C.; relative humidity of 60±15%). All mice had free access to water and standard chow (Provimi Kliba, Kaiseraugst, Switzerland). Four days upon arrival animals were randomized based on body weight and levels of glycated hemoglobin 1c (HbA1c). At 7 weeks of age, animals were treated daily by oral gavage with vehicle (4% methylcellulose) or with Compound A (composed in aqueous 4% methylcellulose) using doses of 1, 3 and 10 mg/kg s.i.d. (doses related to free base). The required dose was applied in a volume of 10 ml/kg body weight. Each dose group consisted of 10 animals. At the end of the treatment period plasma samples were isolated for determination of HbA1c levels. All experimental procedures were conducted according to the German Animal Protection Law.

HbA1c

HbA1c was analyzed from tail-tip-blood (HbA1c determination before treatment) as well as from blood collected from the retro-orbital venous plexus (HbA1c determination after 4 weeks treatment) using the Hemoglobin A1c Test (Siemens, Bad Nauheim, Germany).

Statistical analysis: Values are presented as means±SEM. Statistical differences were determined using one-way-ANOVA followed by a post-hoc analysis with Dunnet's correction (GraphPad Prism).

Definition of significance: n.s.=not significant (p>0.05), *, , *=p<0.05, <0.01, <0.001

Figure 9:
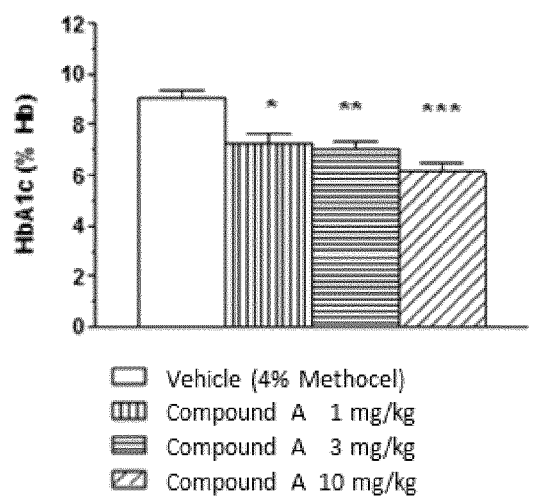
FIG. 9: Effect of Compound A on HbA1c levels in female db/db mice after 28 days oral treatment

Results: Treatment with Compound A significantly and strongly reduced HbA1c levels dose dependently at all doses tested. HbA1c levels were reduced from 9.06% (control) to 7.27 (p<0.05), 7.06 (p<0.01) and 6.16% (p<0.001) at doses of 1, 3, and 10 mg/kg of Compound A (FIG. 9).

| HbA1c levels in female db/db mice after 28 days oral treatment with Compound A (n = 10; doses related to free base). | | |
|---|---|---|
| | dose (mg/kg) | mean HbA1c (%) |
| vehicle | | 9.06 |
| Compound A | 1 | 7.27* |
| | 3 | 7.06** |
| | 10 | 6.16*** |

5. Compound A—Effect on Insulin Sensitivity in Oblob Mice after 29 Days Treatment Model Description Male 5 weeks old ob/ob mice (B6.Cg-Lep$^{ob}$/J, genotype: Lep$^{ob}$/Leb$^{ob}$) and age-matched male lean mice (B6.Cg-Lep$^{ob}$/J, genotype: Lep$^{ob/+}$ * or Leb$^{+/+}$) were purchased from Charles River Laboratories, Japan Inc. All mice were fed with a normal chow (CE-2, CLEA Japan) and allowed free access to tap water. The animals were housed in a room with controlled temperature (23±1° C.), humidity (55±10%) and lightning (lights from 07:00 to 19:00). All experiments were approved by the Institutional Animal Care and Use Committee of Shonan Research Center, Takeda Pharmaceutical Company ltd (Japan).

Experimental Protocol/Measurements

All mice were housed individually in animal cages and used for the study at 7 weeks of age after 2 weeks of acclimation period. Blood samples were collected from the tail vein. Heparin and 2%-EDTA were used to inhibit the coagulation of the blood. Plasma was obtained by centrifugation. Plasma levels of glucose were measured using the automatic analyzer 7180 (Hitachi, Japan). Vehicle (0.5 w/v % methylcellulose, 10 ml/kg) and Compound A (3 and 10 mg/kg suspended in 0.5% methylcellulose solution) were orally administered once daily. After 28 days of administration, the insulin tolerance test (ITT) was performed. Mice were fasted for 6 h and then intraperitoneally administered with insulin (Novolin R, NovoNordisk) at a dose of 0.5 unit/5 ml/kg. Blood samples were collected from tail vein before and 15, 30, 60 and 120 min after the insulin administration. Plasma glucose (PG) level and ITT were measured using the method described above. For the assessment of the insulin sensitivity, plasma glucose levels at 60 min after insulin administration, $AUC_{0-120\ min}$ of plasma glucose level, and changes in plasma glucose level (from the zero time value) at 60 min after insulin administration were used. $AUC_{0-120}$ min of plasma glucose level was calculated using the following formula; [{(0 min PG)+(15 min PG)}×15+{

(15 min PG)+(30 min PG)}×15+{(30 min PG)+(60 min PG)}×30+{(60 min PG)+(20 min PG)}×60]/2.

Statistical Analysis

Data are expressed as mean and standard deviation (n=8 for ob/ob mice and n=5 for lean mice). The dose response trends of Compound A were assessed by one-tailed Williams' test or Shirley-Williams test. The p-values less than 0.025 were considered statistically significant in one-tailed Williams' test or Shirley Williams test. For evaluation of the effects of pioglitazone, statistical differences between vehicle and pioglitazone treated groups were analyzed with Student's t-test or Aspin-Welsh test. The P-values less than 0.05 were considered statistically significant in Student's t-test and Aspin-Welsh test.

Results

To assess the insulin sensitivity, ITT was performed after 29 days treatment. The insulin (0.5 unit/kg, i.p.)—stimulated plasma glucose (PG) reduction was impaired in vehicle treated ob/ob mice compared to lean mice (FIG. 10), suggesting the presence of insulin resistance of ob/ob mice. Treatment with Compound A at 10 mg/kg/day significantly enhanced the insulin-stimulated PG reduction at 60 min compared to vehicle group (FIG. 10A). In addition, Compound A (3 and 10 mg/kg/day) dose-dependently decreased AUC of PG level with statistical significance at 10 mg/kg/day (FIG. 10B). Furthermore, the declines in plasma glucose level at 60 min from the zero time value were significantly greater with Compound A (3 and 10 mg/kg/day)-treated groups compared to vehicle group (FIG. 10C). These results indicate that Compound A improved insulin sensitivity in ob/ob mice.

6. Compound A—Effect on Liver Lipidosis/Liver Weight—8 Weeks Treatment in Diet Induced Obese (DIO) Mice Model Description Obesity was induced in male C57BL/6J mice (Charles River, Germany; 6 weeks of age weighing 19-20 g at start of study) by feeding a high caloric diet (60% kcal % fat; No. 2127; Provimi-Kliba, Switzerland)) for 7 weeks. Animals were single housed in Makrolon cages type II-Long with free access to food and tap water. When body weight gain exceeded 50% compared to body weight at onset of diet, the animals were randomized according to body weight (day −4) followed by treatment for 8 weeks with daily doses of Compound A (0.3, 1, 3 and 10 mg/kg/day, p.o; dissolved in 4% (w/v) aqueous methocel solution to give the required dose in a volume of 10 mL/kg body weight; n=10 in each group). After 8 weeks of treatment, animals were sacrificed. Liver was removed, weighed and fixed in 4% neutral buffered formalin for 2 days, embedded in paraffine and stained with Hematoxylin-Eosin for histological evaluation. The slides were blinded for histological reading and liver lipidosis was evaluated by light microscopy.

The degree of liver lipidosis was assessed semi-quantitatively by the following grading criteria:

Grade 1 (minimal): small round cytoplasmic vacuoles within hepatocytes

Grade 2 (mild): small to medium sized round cytoplasmic vacuoles within hepatocytes Grade 3 (moderate): in addition: round cytoplasmic vacuoles, partly forcing the nucleus to the periphery of the cell Grade 4 (marked): in addition: whole lobe affected For focal changes or multifocal changes 0.5 or 0.25 were subtracted respectively. The mean severity index was calculated by dividing the sum of all gradings/group by the number of animals/group.

Results

Liver Weight

Feeding high caloric diet slightly increased the liver weight of overnight fasted male C57BL/6J mice. Liver weighed 0.96 g and 1.04 g in animals on standard and high caloric diet, respectively (p>0.05). The increase in liver weight was dose-dependently slowed down by Compound A, and abolished at 3 and 10 mg/kg resulting in a level of 0.96 g, respectively 0.95 g.

In summary, feeding high caloric diet resulted in a slight increase in liver weight by 8% compared to standard diet. Treatment with Compound A at 3 and 10 mg/kg completely abolished the increase in liver weight.

TABLE

Effect on Liver weight (Day 56)

| | Liver weight (g) | SEM |
|---|---|---|
| Vehicle standard diet | 0.96 | 0.04 |
| Vehicle high caloric diet | 1.04 | 0.03 |
| Compound A (0.3 mg/kg p.o.) | 1.08 | 0.03 |
| Compound A (1.0 mg/kg p.o.) | 1.01 | 0.03 |
| Compound A (3.0 mg/kg p.o.) | 0.96 | 0.01 |
| Compound A (10 mg/kg p.o.) | 0.95 | 0.02 |

Liver Lipidosis

Figure 11:
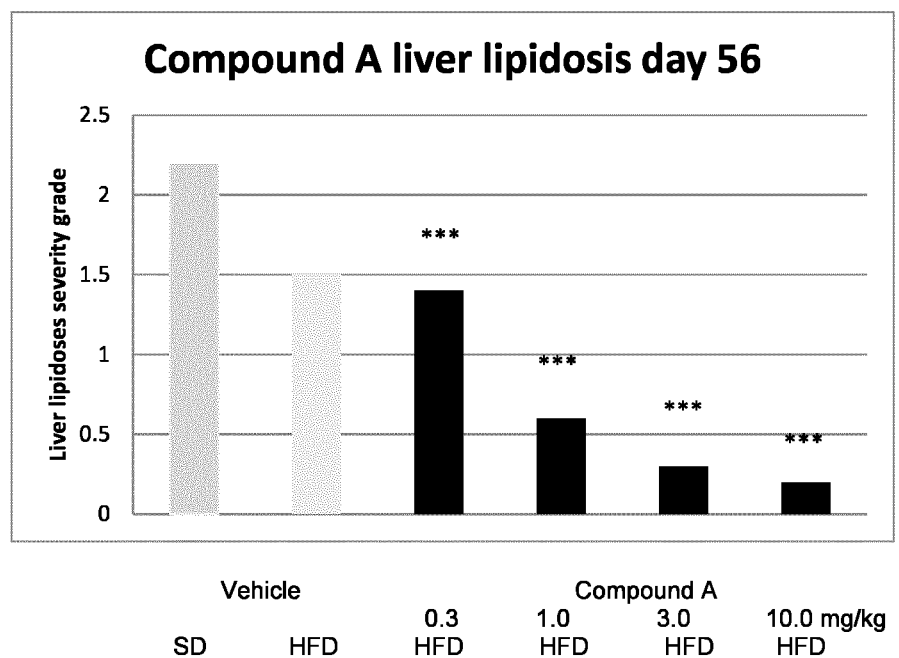
FIG. 11: Liver lipidosis of male C57BL/6J mice on high caloric or standard diet before and after 56 days of once daily administration of Compound A

At day 56, control animals on standard diet (SD) showed mild liver lipidosis (severity grade of 2.2) and control animals on high caloric diet (HD) showed minimal to mild liver lipidosis (severity grade of 1.5). Treatment with Compound A dose-dependently improved liver morphology resulting in severity grades of 1.4, 0.6, 0.3 and 0.2 (0.3, 1, 3, and 10 mg/kg dose, respectively). In summary, treatment with Compound A at doses of 3 and 10 mg/kg almost abolished liver lipidosis (FIG. 11).

TABLE

Effect on Liver Lipidosis

| Compound | Dose (mg/kg) | Grade Liver Lipidosis (mean) | SEM |
|---|---|---|---|
| Vehicle, standard diet (SD) | 0 | 2.2 | 0.25 |
| Vehicle, High caloric diet (HD) | 0 | 1.5 | 0.44 |
| Compound A, HD | 0.3 | 1.4 | 0.29 |
| Compound A, HD | 1.0 | 0.6 | 0.29 |
| Compound A, HD | 3.0 | 0.3 | 0.21 |
| Compound A, HD | 10.0 | 0.2 | 0.08 |

7. Compound A—Anti-Fibrotic Activity in Human Hepatic Stellate Cells

The effect on human stellate cells (HSCs) activation was evaluated by gene expression of alfa smooth muscle actin (αSMA) induced by TGF-β.

Primary HSCs (ScienCell) were suspended in serum-free SteCM medium (ScienCell) and seeded on Poly-D-Lysine-coated 96 well plates as $2.5 \times 10^3$ cells/100 uL/well. Six hours after the seeding, HSCs were treated with Compound A (0, 0.0001, 0.001, 0.01, 0.1, and 1 μM), TGF-β (0.2 ng/mL) and forskolin (1 μM) for 24 hours. After the 24-hours incubation, total RNA was extracted from cell lysate using RNeasy 96 Kit (QIAGEN 74182). cDNA was amplified using High-Capacity cDNA Reverse Transcription Kit (ABI 4368813), and target gene mRNA was measured using Taqman PCR. The target gene expression level was normalized by GAPDH. The experiment was repeated 5 times.

Results

Figure 12:
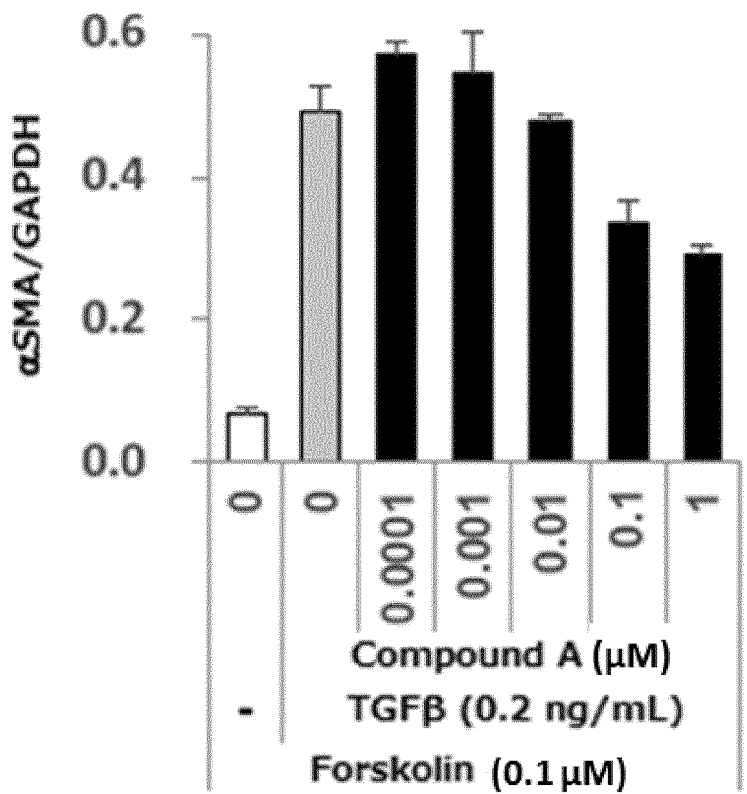
FIG. 12: Anti-fibrotic activity of Compound A in human hepatic stellate cells

In the presence of forskolin, Compound A dose-dependently suppressed TGF-β-induced αSMA gene expression in HSCs. Results are shown by mean±SD in FIG. 12.

8. Compound A—Systemic Anti-Inflammatory Effect In Vitro and In Vivo a) Anti-Inflammatory Effect of Compound A in THP-1 Cells (In Vitro)

Anti-inflammatory effect of Compound A was evaluated by gene expression of TNFα induced by LPS in THP-1 cells, a human monocytic cell line.

THP-1 cells (ATCC) were suspended in RPMI medium containing 10% FBS and 50 ng/mL PMA ($2.5 \times 10^5$ cells/mL) and seeded on 96 well plates. Fourty-eight hours after the seeding, the medium was exchanged to serum-free RPMI medium. Three hours after the exchange, Compound A (0, 0.0001, 0.001, 0.01, 0.1 and 1 μM), LPS (1 ng/mL), and forskolin (0.1 μM) were added to the THP-1 cells. After the 5-hours incubation, total RNA was extracted from cell lysate using RNeasy 96 Kit (QIAGEN 74182). cDNA was amplified using High-Capacity cDNA Reverse Transcription Kit (ABI 4368813), and target gene mRNA was measured using Taqman PCR. The target gene expression level was normalized by GAPDH. The experiment was repeated 5 times.

Results

Figure 15:
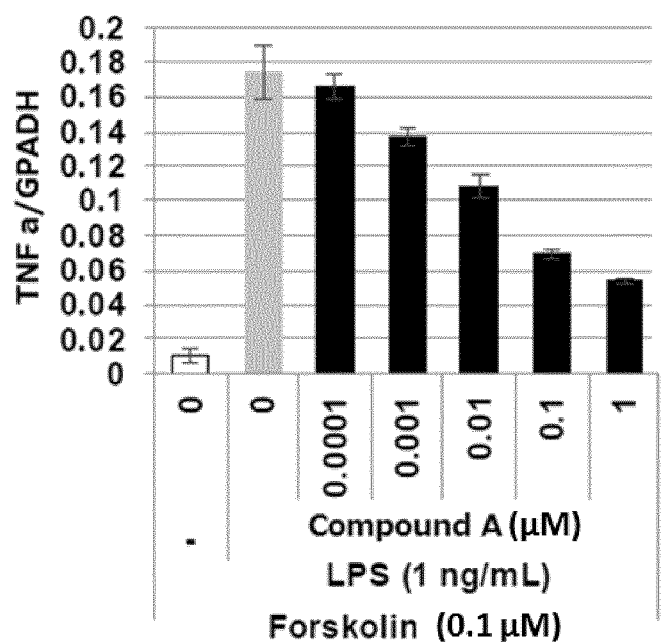
FIG. 15: Anti-fibrotic activity of Compound A in human THP-1 cells

In the presence of forskolin, Compound A dose-dependently suppressed LPS-induced TNF-α gene expression in THP-1 cells. Results are shown by mean±SD in FIG. 15.

b) Anti-Inflammatory Effect of Compound A (In Vivo)—Effect of Compound A on Systemic Tumor Necrosis Factor Alpha (TNFα) Release in Lipopolysaccharide (LPS)-Challenged Spraque Dawley (SD) Rats Compound A was administered 1 h before LPS challenge at doses of 0.1, 0.3, 1, 3 and 10 mg/kg (n=8 animals per dose group). An LPS and vehicle treated control group of n=8 animals was enclosed. Compound A or vehicle was given per os (p.o.) by gavage (administration volume: 10 mL/kg b.w.). LPS was injected intravenously (i.v.) at a dose of 20 μg/kg (administration volume: 1 mL/kg b.w.) 1 h after compound or vehicle administration.

One hour after LPS-challenge, the animals were sacrificed by inhalative isoflurane anaesthesia (5%; flow rate: 2-3 L/min) and subsequent cervical dislocation. Heparinized blood was obtained by heart puncture. Blood was centrifuged (21,000×g, 4° C., 10 min), and plasma samples were kept frozen at −20° C. until determination of TNFα levels by ELISA.

Results

Figure 16:
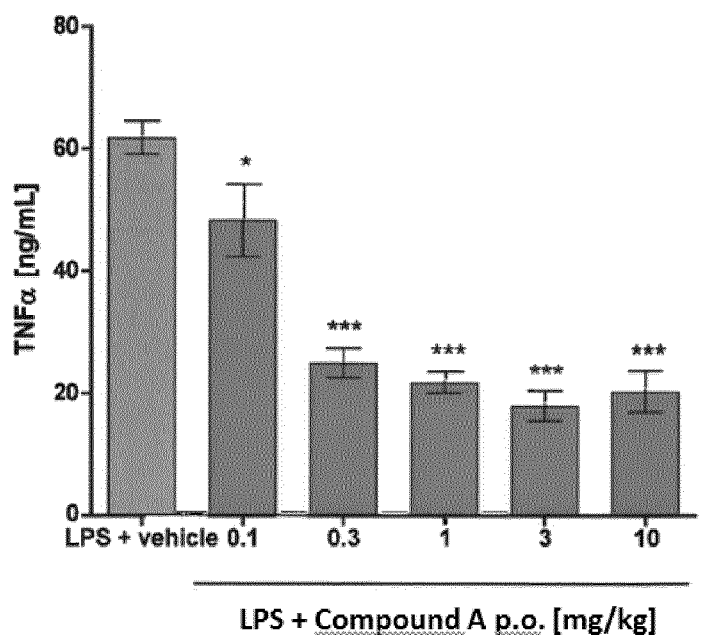
FIG. 16: Effect of Compound A on concentration of TNFα in plasma samples of LPS challenged Sprague Dawley rats

Compound A dose-dependently reduced the mean TNFα in blood plasma compared to the vehicle-treated control. The reduction in the TNFα concentration was statistically significant at all doses tested. Results are shown by mean±SD in FIG. 16. (Statistics: One-Way ANOVA with Dunnett's Post-Test, *P<0.05, P<0.01 and *P<0.001 vs. vehicle control)

The results provided under 8a) and 8b) together with the results of suppression of hepatic inflammatory TNFα gene expression provided under 1) clearly demonstrate the capability of Compound A to exert systemic anti-inflammatory effects as well as anti-inflammatory effects in the liver.

Further Aspects of the Invention:
a) Use of a phosphodiesterase 4 (PDE4) inhibitor for the manufacture of a pharmaceutical composition for the treatment of a disease selected from non-alcoholic fatty liver disease (NAFLD) and non-alcoholic steato-hepatitis (NASH), wherein the phosphodiesterase 4 (PDE4) inhibitor is selected from the group consisting of Compound A and a pharmaceutically acceptable salt thereof.
b) Use of a phosphodiesterase 4 (PDE4) inhibitor according to a), wherein the disease is non-alcoholic fatty liver disease (NAFLD).
c) Use of a phosphodiesterase 4 (PDE4) inhibitor according to a), wherein the disease is non-alcoholic steato-hepatitis (NASH).
d) Use of a phosphodiesterase 4 (PDE4) inhibitor for the manufacture of a pharmaceutical composition for the concomitant treatment of diabetes mellitus type 2 and non-alcoholic fatty liver disease (NAFLD), wherein the phosphodiesterase 4 (PDE4) inhibitor is selected from the group consisting of Compound A and a pharmaceutically acceptable salt thereof.
e) Use of a phosphodiesterase 4 (PDE4) inhibitor for the manufacture of a pharmaceutical composition for the concomitant treatment of diabetes mellitus type 2 and non-alcoholic steato-hepatitis (NASH), wherein the phosphodiesterase 4 (PDE4) inhibitor is selected from the group consisting of Compound A and a pharmaceutically acceptable salt thereof.
f) Use according to any one of a) to e), wherein the phosphodiesterase 4 (PDE4) inhibitor is Compound A.
g) Use according to any one of a) to e), wherein Compound A is to be administered once daily at a dose of between 0.1 and 6 mg or a pharmaceutically acceptable salt of Compound A is to be administered once daily at a dose corresponding to the Compound A once daily dose of between 0.1 and 6 mg.
h) Use according to f), wherein Compound A is to be administered once daily at a dose of between 0.1 and 6 mg.
i) Use according to any one of a) to e), wherein Compound A is to be administered twice daily at a dose of between 0.1 and 6 mg or a pharmaceutically acceptable salt of Compound A is to be administered twice daily at a dose corresponding to the Compound A twice daily dose of between 0.1 and 6 mg.
j) Use according to f), wherein Compound A is to be administered twice daily at a dose of between 0.1 and 6 mg.
k) Use according to any one of a) to e), wherein Compound A is to be administered three times a day at a dose of between 0.1 and 6 mg or a pharmaceutically acceptable salt of Compound A is to be administered three times a day at a dose corresponding to the Compound A three times a day dose of between 0.1 and 6 mg.
l) Use according to f), wherein Compound A is to be administered three times a day at a dose of between 0.1 and 6 mg.
m) Use according to any one of a) to e), wherein Compound A is to be administered once daily at a dose selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg or the pharmaceutically acceptable salt of Compound A is to be administered once daily at a dose corresponding to a Compound A once daily dose selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg.
n) Use according to f), wherein Compound A is to be administered once daily at a dose selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg.
o) Use according to any one of a) to e), wherein Compound A is to be administered twice daily at a dose selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg or the pharmaceutically acceptable salt of Compound A is to be administered twice daily at a dose corresponding to a Compound A twice daily dose selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg.
p) Use according to f), wherein Compound A is to be administered twice daily at a dose selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg.
q) Use according to any one of a) to e), wherein Compound A is to be administered three times a day at a dose selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg or the pharmaceutically acceptable salt of Compound A is to be administered three times a day at a dose corresponding to a Compound A three times a day dose selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg.
r) Use according to f), wherein Compound A is to be administered three times a day at a dose selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg.
s) Use according to any one of a) to e), wherein Compound A is to be administered once daily at a dose of between 0.8 and 3.25 mg or a pharmaceutically acceptable salt of Compound A is to be administered once daily at a dose corresponding to the Compound A once daily dose of between 0.8 and 3.25 mg.
t) Use according to f), wherein Compound A is to be administered once daily at a dose of between 0.8 and 3.25 mg.
u) Use according to any one of a) to e), wherein Compound A is to be administered twice daily at a dose of between 0.8 and 3.25 mg or a pharmaceutically acceptable salt of Compound A is to be administered twice daily at a dose corresponding to the Compound A twice daily dose of between 0.8 and 3.25 mg.
v) Use according to f), wherein Compound A is to be administered twice daily t a dose of between 0.8 and 3.25 mg.
w) Use according to any one of a) to e), wherein Compound A is to be administered three times a day at a dose of between 0.8 and 3.25 mg or a pharmaceutically acceptable salt of Compound A is to be administered three times a day at a dose corresponding to the Compound A three times a day dose of between 0.8 and 3.25 mg.
x) Use according to f), wherein Compound A is to be administered three times a day at a dose of between 0.8 and 3.25 mg.
y) Use according to any one of a) to e), wherein Compound A is to be administered once daily at a dose selected from 0.8, 0.9, 1, 1.25, 1.5, 1.75, 2, 2.25, 2.5, 2.75, 3 and 3.25 mg or the pharmaceutically acceptable salt of Compound A is to be administered once daily at a dose corresponding to a Compound A once daily dose selected from 0.8, 0.9, 1, 1.25, 1.5, 1.75, 2, 2.25, 2.5, 2.75, 3 and 3.25 mg.
z) Use according to f), wherein Compound A is to be administered once daily at a dose selected from 0.8, 0.9, 1, 1.25, 1.5, 1.75, 2, 2.25, 2.5, 2.75, 3 and 3.25 mg.
aa) Use according to any one of a) to e), wherein Compound A is to be administered twice daily at a dose selected from 0.8, 0.9, 1, 1.25, 1.5, 1.75, 2, 2.25, 2.5, 2.75, 3 and 3.25 mg or the pharmaceutically acceptable salt of Compound A is to be administered twice daily at a dose corresponding to a Compound A twice daily dose selected from 0.8, 0.9, 1, 1.25, 1.5, 1.75, 2, 2.25, 2.5, 2.75, 3 and 3.25 mg.
bb) Use according to f), wherein Compound A is to be administered twice daily at a dose selected from 0.8, 0.9, 1, 1.25, 1.5, 1.75, 2, 2.25, 2.5, 2.75, 3 and 3.25 mg.
cc) Use according to any one of a) to e), wherein Compound A is to be administered three times a day at a dose selected from 0.8, 0.9, 1, 1.25, 1.5, 1.75, 2, 2.25, 2.5, 2.75, 3 and 3.25 mg or the pharmaceutically acceptable salt of Compound A is to be administered three times a day at a dose corresponding to a Compound A three times a day dose selected from 0.8, 0.9, 1, 1.25, 1.5, 1.75, 2, 2.25, 2.5, 2.75, 3 and 3.25 mg.
dd) Use according to f), wherein Compound A is to be administered three times a day at a dose selected from 0.8, 0.9, 1, 1.25, 1.5, 1.75, 2, 2.25, 2.5, 2.75, 3 and 3.25 mg.
ee) Use according to any one of a) to e), wherein Compound A is to be administered once daily at a dose of between 0.1 and 2 mg or the pharmaceutically acceptable salt of Compound A is to be administered once daily at a dose corresponding to a Compound A once daily dose of between 0.1 mg and 2 mg.
ff) Use according to f), wherein Compound A is to be administered once daily at a dose of between 0.1 mg and 2 mg.
gg) Use according to any one of a) to e), wherein Compound A is to be administered once daily at a dose selected from 0.1, 0.2, 0.25, 0.3, 0.4, 0.5, 0.6, 0.7, 0.75, 0.8, 0.9, 1, 1.25, 1.5, 1.75 and 2 mg or the pharmaceutically acceptable salt of Compound A is to be administered once daily at a dose corresponding to a Compound A once daily dose selected from 0.1, 0.2, 0.25, 0.3, 0.4, 0.5, 0.6, 0.7, 0.75, 0.8, 0.9, 1, 1.25, 1.5, 1.75 and 2 mg.
hh) Use according to f), wherein Compound A is to be administered once daily at a daily dose selected from 0.1, 0.2, 0.25, 0.3, 0.4, 0.5, 0.6, 0.7, 0.75, 0.8, 0.9, 1, 1.25, 1.5, 1.75 and 2 mg.
ii) Pharmaceutical composition comprising a phosphodiesterase 4 (PDE4) inhibitor for use in the treatment of a disease selected from non-alcoholic fatty liver disease (NAFLD) and non-alcoholic steato-hepatitis (NASH), wherein the phosphodiesterase 4 (PDE4) inhibitor is selected from the group consisting Compound A and a pharmaceutically acceptable salt thereof.
jj) Pharmaceutical composition according to ii), wherein the disease is non-alcoholic fatty liver disease (NAFLD).
kk) Pharmaceutical composition according to ii), wherein the disease is non-alcoholic steato-hepatitis (NASH).
ll) Pharmaceutical composition comprising a phosphodiesterase 4 (PDE4) inhibitor for use in the concomitant treatment of diabetes mellitus type 2 and non-alcoholic fatty liver disease (NAFLD), wherein the phosphodiesterase 4 (PDE4) inhibitor is selected from the group consisting of Compound A and a pharmaceutically acceptable salt thereof.

mm) Pharmaceutical composition comprising a phosphodiesterase 4 (PDE4) inhibitor for use in the concomitant treatment of diabetes mellitus type 2 and non-alcoholic steato-hepatitis (NASH), wherein the phosphodiesterase 4 (PDE4) inhibitor is selected from the group consisting of Compound A and a pharmaceutically acceptable salt thereof.

nn) Pharmaceutical composition according to any one of ii) to mm), wherein the phosphodiesterase 4 (PDE4) inhibitor is Compound A.

oo) Pharmaceutical composition according to any one of ii) to mm), wherein Compound A is to be administered once daily at a dose of between 0.1 mg and 2 mg or a pharmaceutically acceptable salt of Compound A is to be administered once daily at a dose corresponding to a Compound A once daily dose of between 0.1 mg and 2 mg.

pp) Pharmaceutical composition according to nn), wherein Compound A is to be administered once daily at a dose of between 0.1 mg and 2 mg.

qq) Pharmaceutical composition according to any one of ii) to mm), wherein Compound A is to be administered once daily at a dose selected from 0.1, 0.2, 0.25, 0.3, 0.4, 0.5, 0.6, 0.7, 0.75, 0.8, 0.9, 1, 1.25, 1.5, 1.75 and 2 mg or a pharmaceutically acceptable salt of Compound A is to be administered once daily at a dose corresponding to a Compound A once daily dose selected from 0.1, 0.2, 0.25, 0.3, 0.4, 0.5, 0.6, 0.7, 0.75, 0.8, 0.9, 1, 1.25, 1.5, 1.75 and 2 mg.

rr) Pharmaceutical composition according to nn), wherein Compound A is to be administered once daily at a dose selected from 0.1, 0.2, 0.25, 0.3, 0.4, 0.5, 0.6, 0.7, 0.75, 0.8, 0.9, 1, 1.25, 1.5, 1.75 and 2 mg.

ss) A method for the treatment of non-alcoholic fatty liver disease (NAFLD) in a mammal in need thereof, which comprises administering to a mammal suffering from non-alcoholic fatty liver disease (NAFLD), a therapeutically effective amount of a phosphodiesterase 4 (PDE4) inhibitor, wherein the phosphodiesterase 4 (PDE4) inhibitor is selected from the group consisting of Compound A and a pharmaceutically acceptable salt thereof.

tt) A method for the treatment of non-alcoholic steato-hepatitis (NASH) in a mammal in need thereof, which comprises administering to a mammal suffering from non-alcoholic steato-hepatitis (NASH), a therapeutically effective amount of a phosphodiesterase 4 (PDE4) inhibitor, wherein the phosphodiesterase 4 (PDE4) inhibitor is selected from the group consisting of Compound A and a pharmaceutically acceptable salt thereof.

uu) A method for the concomitant treatment of diabetes mellitus type 2 and non-alcoholic fatty liver disease (NAFLD) in a mammal in need thereof, which comprises administering to a mammal suffering from diabetes mellitus type 2 and non-alcoholic fatty liver disease (NAFLD), a therapeutically effective amount of a phosphodiesterase 4 (PDE4) inhibitor, wherein the phosphodiesterase 4 (PDE4) inhibitor is selected from the group consisting of Compound A and a pharmaceutically acceptable salt thereof.

vv) A method for the concomitant treatment of diabetes mellitus type 2 and non-alcoholic steato-hepatitis (NASH) in a mammal in need thereof, which comprises administering to a mammal suffering from diabetes mellitus type 2 and non-alcoholic steato-hepatitis (NASH), a therapeutically effective amount of a phosphodiesterase 4 (PDE4) inhibitor, wherein the phosphodiesterase 4 (PDE4) inhibitor is selected from the group consisting of Compound A and a pharmaceutically acceptable salt thereof.

ww) The method according to any one of ss) to vv), wherein the phosphodiesterase 4 (PDE4) inhibitor is Compound A.

xx) The method according to any one of ss) to vv), wherein Compound A is administered once daily at a dose of between 0.1 mg and 2 mg or the pharmaceutically acceptable salt of Compound A is administered once daily at a dose corresponding to a Compound A once daily dose of between 0.1 mg and 2 mg.

yy) The method according to ww), wherein Compound A is administered once daily at a dose of between 0.1 mg and 2 mg.

zz) The method according to any one of ss) to vv), wherein Compound A is administered once daily at a dose selected from 0.1, 0.2, 0.25, 0.3, 0.4, 0.5, 0.6, 0.7, 0.75, 0.8, 0.9, 1, 1.25, 1.5, 1.75 and 2 mg or the pharmaceutically acceptable salt of Compound A is administered once daily at a dose corresponding to a Compound A once daily dose selected from 0.1, 0.2, 0.25, 0.3, 0.4, 0.5, 0.6, 0.7, 0.75, 0.8, 0.9, 1, 1.25, 1.5, 1.75 and 2 mg.

aaa) The method according to ww), wherein Compound A is administered once daily at a dose selected from 0.1, 0.2, 0.25, 0.3, 0.4, 0.5, 0.6, 0.7, 0.75, 0.8, 0.9, 1, 1.25, 1.5, 1.75 and 2 mg.

The invention claimed is:

1. A method for the treatment of non-alcoholic fatty liver disease (NAFLD) in a mammal in need thereof, comprising:
    administering to a mammal suffering from non-alcoholic fatty liver disease (NAFLD), a therapeutically effective amount of a phosphodiesterase 4 (PDE4) inhibitor which is 5-((2R,4aR,10bR)-9-Ethoxy-2-hydroxy-8-methoxy-1,2,3,4,4a,10b-hexahydro-phenanthridin-6-yl)1-methyl-1H-pyridin-2-one or pharmaceutically acceptable salts thereof.

2. A method for the treatment of non-alcoholic steato-hepatitis (NASH) in a mammal in need thereof, which comprises administering to a mammal suffering from non-alcoholic steato-hepatitis (NASH), a therapeutically effective amount of a phosphodiesterase 4 (PDE4) inhibitor which is 5-((2R,4aR,10bR)-9-Ethoxy-2-hydroxy-8-methoxy-1,2,3,4,4a,10b-hexahydro-phenanthridin-6-yl)1-methyl-1H-pyridin-2-one, or pharmaceutically acceptable salts thereof.

3. A method for the concomitant treatment of diabetes mellitus type 2 and non-alcoholic steato-hepatitis (NASH) in a mammal in need thereof, comprising administering to a mammal suffering from diabetes mellitus type 2 and non-alcoholic steato-hepatitis (NASH), a therapeutically effective amount of a phosphodiesterase 4 (PDE4) inhibitor which is 5-((2R,4aR,10bR)-9-Ethoxy-2-hydroxy-8-methoxy-1,2,3,4,4a,10b-hexahydro-phenanthridin-6-yl)1-methyl-1H-pyridin-2-one, or pharmaceutically acceptable salts thereof.

4. The method according to claim 2, wherein the PDE4 inhibitor is 5-((2R,4aR,10bR)-9-Ethoxy-2-hydroxy-8-methoxy-1,2,3,4,4a,10b-hexahydro-phenanthridin-6-yl)1-methyl-1H-pyridin-2-one.

5. The method according to claim 2, wherein the PDE4 inhibitor or its salt is administered once daily at a dose at least 0.1 mg.

6. The method according to claim 4, wherein the PDE4 inhibitor is administered once daily at a dose at least 0.1 mg.

7. The method according to claim 2, wherein the PDE4 inhibitor or its salt is administered twice daily at a dose at least 0.1 mg.

8. The method according to claim 2, wherein the PDE4 inhibitor or its salt is administered three times a day at a dose at least 0.1 mg.

9. The method according to claim 5, wherein the dose of the PDE4 inhibitor or its salt is selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg.

10. The method according to claim 6, wherein the dose of the PDE4 inhibitor is selected from 0.1, 0.2, 0.25, 0.3, 0.4, 0.5, 0.6, 0.7, 0.75, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75 and 6 mg.

11. The method according to claim 2, wherein the PDE4 inhibitor or its salt is administered once daily at a dose at least 0.8 mg.

12. The method according to claim 4, wherein the PDE4 inhibitor is administered once daily at a dose at least 0.8 mg.

13. The method according to claim 2, wherein the PDE4 inhibitor or its salt is administered twice daily at a dose at least 0.8 mg.

14. The method according to claim 2, wherein the PDE4 inhibitor or its salt is administered three times a day at a dose at least 0.8 mg.

15. The method according to claim 11, wherein the dose of the PDE4 inhibitor or its salt is selected from 0.8, 0.9, 1, 1.25, 1.5, 1.75, 2, 2.25, 2.5, 2.75, 3 and 3.25 mg.

16. The method according to claim 12, wherein the dose of the PDE4 inhibitor is selected from 0.8, 0.9, 1, 1.25, 1.5, 1.75, 2, 2.25, 2.5, 2.75, 3 and 3.25 mg.

17. The method according to claim 2, wherein the PDE4 inhibitor or its salt is administered in an oral dosage form.

* * * * *